(12) United States Patent
Aisa

(10) Patent No.: US 10,093,329 B2
(45) Date of Patent: Oct. 9, 2018

(54) TRACK CIRCUIT MECHANICAL JOINT INTEGRITY CHECKER

(71) Applicant: ALSTOM TRANSPORT TECHNOLOGIES, Levallois-Perret (FR)

(72) Inventor: Pier Alessandro Aisa, Granarolo Emilia (IT)

(*) Notice: Subject to any disclaimer, the term of this patent is extended or adjusted under 35 U.S.C. 154(b) by 307 days.

(21) Appl. No.: 14/900,084

(22) PCT Filed: Jul. 26, 2013

(86) PCT No.: PCT/IB2013/056137
§ 371 (c)(1),
(2) Date: Dec. 18, 2015

(87) PCT Pub. No.: WO2015/011529
PCT Pub. Date: Jan. 29, 2015

(65) Prior Publication Data
US 2016/0152251 A1  Jun. 2, 2016

(51) Int. Cl.
*B61L 1/18* (2006.01)
*B61L 1/20* (2006.01)
*B61L 23/04* (2006.01)
*B61L 25/02* (2006.01)
*G01N 27/02* (2006.01)

(52) U.S. Cl.
CPC ............. *B61L 1/18* (2013.01); *B61L 1/187* (2013.01); *B61L 1/188* (2013.01); *B61L 1/20* (2013.01); *B61L 23/04* (2013.01); *B61L 25/02* (2013.01); *G01N 27/02* (2013.01)

(58) Field of Classification Search
CPC .. B61L 1/18; B61L 1/187; B61L 1/188; B61L 1/20; B61L 23/04; B61L 25/02; B61L 23/044; B61L 23/168; G01N 27/02
See application file for complete search history.

(56) References Cited

U.S. PATENT DOCUMENTS

| 6,437,693 | B1* | 8/2002 | Todd | H04L 27/152 340/539.1 |
| 2016/0075356 | A1* | 3/2016 | Kull | B61L 23/044 246/121 |

FOREIGN PATENT DOCUMENTS

| EP | 0 165 048 | * 12/1985 |
| EP | 0165048 A2 | 12/1985 |
| EP | 0952065 A1 | 10/1999 |

(Continued)

*Primary Examiner* — Mark T Le
(74) *Attorney, Agent, or Firm* — Themis Law

(57) ABSTRACT

An electrically insulating mechanical joint checker for mechanical joints connecting rails of following track segments of a railway line, each track segment forming part of a track circuit. The track segment includes electric signal transmitting units and receiving units for transmitting and receiving train presence detection signals within the track segment and/or relating communication signals between the train and the track segment. The train presence detection signals and communication signals include a further joint detection signal, generated and transmitted by the transmitting units and received by the receiving units belonging to the same track segment, the joint detection signal relating to the track segment being different at least in respect to the one relating to the adjacent track segments. A method to detect a failure or breakage of a mechanical joint inside a track segment is also disclosed.

12 Claims, 3 Drawing Sheets

(56) References Cited

FOREIGN PATENT DOCUMENTS

GB 2063539 A 6/1981
WO WO2010023543 A2 3/2010

* cited by examiner

TRACK CIRCUIT MECHANICAL JOINT INTEGRITY CHECKER

FIELD OF THE INVENTION

The invention relates to a mechanical joint checker for track circuits.

The scope of the invention is to monitor rail joints in order to detect their breakage and to avoid track circuit failures and prevent derailments.

BACKGROUND OF THE INVENTION

Generally speaking rail signalling systems are designed and implemented to allow the safe passage of trains throughout the railway network. Track circuits play a major role within the interlocking as they indicate the presence of a rail vehicle and can exchange data speed information with rail vehicles. Track circuits can be divided into two groups: "jointless" track circuits and track circuits separated by mechanical insulated joints, this invention is particularly directed to the second type.

These insulated joints enable isolated sections of rails to be used as part of the track circuits.

The track circuits play a vital role, and it is therefore important to be able to identify any faulty components.

In particular if a failure of a mechanical joint occurs, the track segment won't be isolated no more, causing the signal communication between the track segment and the adjacent one. Moreover adjacent rails can be no more aligned between each other causing risk of derailments.

Consequently the track circuit will be composed by track segments in communication, bringing to dangerous and unsafe situations.

First of all it is in fact imperative that a rail break can be detected in time because it could cause a significant failure, such as a derailment, especially in the case of curved track sections.

Furthermore, if a communication between two adjacent track segments occurs, the track circuit will be unable to monitor the presence of a train in a track segment due to the impossibility to detect the shunt resistance of the train axle and wrong information on speed data can be propagated to the train.

The breakage of a mechanical joint causes drawbacks not only relating to the high-frequency signals (train detection) in the track circuit, but also relating to the low-frequency signal, because trains can acquire wrong speed data.

As it can be appreciated by the discussion above, an efficient monitoring and detection of the failure of mechanical joints covers a fundamental aspect in the safety of railway track circuits.

A possible solution is disclosed in the document EP 2216229 relating to a device for monitoring an insulated joint between sections of rail comprising a monitoring arrangement for monitoring current flow between two points along a rail in the vicinity of the rail joint by measuring voltages at the two points.

The document U.S. Pat. No. 6,779,761 describes a detection of a break in a rail by connecting the two rails together electrically with two electrical connections at opposite ends of a section of the line, causing electrical currents to flow in parallel along the two rails from a current source and detecting the currents flowing in each of the rails. From the two values of current it is possible to find if there is a break in one of the rails.

Usually the solution presented in the prior art documents relates to a method of using the effects of the changes in the track circuit introduced by the break on a testing signal.

Coded DC, or AC signals or pulsed signals are also used and they are fed to the track circuits by transmitters at one end and received by receivers at the other end of the track circuit.

Furthermore the devices and methods belonging to the state of the art provide a processing unit carrying out processing of the received signals for determining if the variations are due to a break.

Independently from the solution adopted, the known devices and methods present dedicated products to detect the breakings of mechanical joint, that must be installed in the track circuit.

The use of dedicated devices brings functional and economical drawbacks.

From a functional point of view, the addition of one or more components to the track circuit increases the possibility of failures of the track circuit and it requires more controls.

The economical drawbacks are obvious since there is an increase of costs, due not only to the purchase of a specific product, but also to the maintenance required.

Therefore, there is still the need for a track circuit in which the detection of a mechanical joint failure or breakage is integrated within the train detection function itself and therefore can be detected in an efficient way, without incurring in expensive costs and/or complex configurations using specific components added to the ones belonging to the track circuit.

SUMMARY OF THE INVENTION

The present invention fulfils such need by providing a mechanical joint checker as described hereinafter.

Due to the fact that the joint insulation integrity signal defines univocally the track segment to which it refers, the receiving units belonging to a determinate track segment preventively know the joint insulation integrity signal.

In particular the analyzing unit compare the values of the characteristic parameters of the joint insulation integrity signal received with the predetermined values of the joint integrity system, that defines the track segment to which the receiving units belong.

Consequently if a receiving units receives a joint insulation integrity signal different from the one relating to the track segment to which the receiving units belong, a loss of insulation occurs.

This loss of insulation can be imputed to the failure of one of the mechanical joints relating to the track segment.

As usual when such condition appears, an alarm signal can be sent to remote operating unit and automatically the track segment is put in a safety condition, in occupied status.

For this reason, according to a preferred embodiment, means for setting the track circuit in a safety conditions are provided.

As it clearly appears, the solution presented is fully integrated in the track circuit components, because the joint insulation integrity signal is generated and transmitted by the transmitting units and received by the receiving units.

The invention solves the safety hazard related to failures and breakings of insulated mechanical joints and it can detect such breakings in all conditions, with all codes injected on it.

Furthermore, the invention removes in an efficient way the safety hazard related to failures of power supply that can lead to an undetected train axle on track circuit products, by use an additional super imposed frequency to detect the breaking of the mechanical joints.

The unique correspondence between each track segment and a corresponding joint insulation integrity signal avoid errors in the detection of a failure of mechanical joints.

Consequently, according to the described configuration, in order to declare clear, no absence of train or the like, a track segment and to generate signals to be transmitted to the train, the mechanical joint checker of the present invention, will look not only at the nominal signal coming from the track segment, but also will look at an additional superimposed frequency, in order to discriminate the breaking of the mechanical joint.

In respect of the prior art documents and disclosed solutions, the track circuit of the present invention do not requires traditional measurements or processing of the signals for determining the break, such as comparison with thresholds or the like, but the invention automatically avoids errors in the transmission of messages to trains due to joint breaks between two adjacent blocks.

The aim of the following features and of the possible embodiments of the mechanical joint checker belonging to the present invention is to improve the detection of the joint insulation integrity signal, avoiding distortion of the same and also avoiding that the frequency signals currently transmitted in the track segment are disturbed by the transmission of the joint insulation integrity signal.

According to a further embodiment, the transmitting units comprise a signal generation unit to generate and to transmit the said joint insulation integrity signal and the receiving units comprise an analyzing unit that compares the received joint insulation integrity signal with the one that identifies the track segment.

Advantageously the joint insulation integrity signal is a digital signal comprising a bit coded message.

In this case the analyzing unit will compare the values of the bits of the message received with the ones that defines the track segment to which the receiving units belong.

The choice of the modulation and of the additional frequency is made by guarantying that will not be interpreted by trains on-board equipment and that will be immune versus noises produced by trains or substations.

According to an improvement of the present invention, the transmitting units comprise timing means, which timing means activate the signal generation unit according to pre-determined timing rules.

This timing rules are determined in order to maintain at the lowest level the tension spikes of the entire system.

In fact, the train presence detection signals and communication signals are constituted by a wave, which presents an amplitude maximum value and an amplitude minimum value.

The generation unit is activated by the timing means during the time interval of amplitude minimum value.

This important feature allows to decide when the joint insulation integrity signal is generated, setting the timing rules in the desired manner.

Preferably the joint insulation integrity signal presents a carrier frequency of 500 Hz, including the signal generation unit means to generate carrier waves.

This frequency don't present disturbs created both by the other frequency signals and by the train that transit in the track segment.

According to another embodiment, the joint insulation integrity signal is obtained by a Frequency-shift keying modulation, in which the bit with value "1" presents a carrier frequency of 525 Hz while the bit with value "0" presents a carrier frequency of 475 Hz.

This modulation and the choice of the two carrier frequencies is due to the necessity to simplify the design features, maintaining an efficient detection and reception of the joint insulation integrity signal.

The FSK (Frequency-shift keying) modulation of the joint insulation integrity signal, according to the present invention, presents preferably a modulation index equal to 1, in order to reach a bit-rate equal to the frequency deviation.

The difference between the carrier frequency of the bit with value "1" and the carrier frequency of the bit with value "0" is 50 Hz, so the joint insulation integrity signal will be transmitted with a bit rate equal to 50 bit/sec.

The result achieved with this important feature is a "clean" emission spectrum that allow an efficient reconstruction of the signal, avoiding distortion of the same.

Furthermore, due to the chosen values, the passage from the bit with value "1" to the bit with value "0" corresponds to a zero of the sinusoid, which consequently don't present phase discontinuity.

The aim is to simplify the configuration of the track circuit and above all of the power amplifiers belonging to it.

Advantageously, the joint insulation integrity signal is a bit coded message composed by 8 bit.

The number of bit that identifies the signal of interest has been chosen in order to obtain a compromise between the total length of the message and the range of time in which the message is transmitted.

A message composed by 8 bit can be transmitted in a quite short time and 8 bits allow to create a certain number of messages that presents an Hamming distance equal to 3, as described below, between two messages belonging to the same track segment, which has to be compared.

Consequently, in this case the 8 bit messages maximize the difference between them and they minimize the errors in the detection of the correct code.

The present invention relates also to a method to detect a failure or breakage of a mechanical joint connecting rails of following track segments of a railway line, each track segment forming part of a track circuit.

Each track segment presents electric signal transmitting units and receiving units for transmitting and receiving train presence detection signals relating within said track segment and/or relating communication signals between the train and the track segment.

The method provides the step of:
a) generation of a further joint insulation integrity signal by the transmitting units, which joint insulation integrity signal is associated to each track segment. The joint insulation integrity signal relating to the track segment is different at least in respect to the one relating to the adjacent track segments, concerning to characteristic parameters uniquely identifying the joint insulation integrity signal of each track segment;
b) transmission of the joint insulation integrity signal by the transmitting units;
c) reception of the joint insulation integrity signal by the receiving units;
d) comparison of the received joint insulation integrity signal with the one that identifies the track segment by the receiving units;
e) set of the said track segment (11) in a occupied status.

The transmitting units and the receiving units belong to the same track segment.

Therefore each track segment is identified with a different joint insulation integrity signal, if the receiving units receive a joint insulation integrity signal relating to a track segment different from the one they belong, it means that a loss of insulation happened in the track segment.

Preferably the joint insulation integrity signal is a digital signal comprising a bit coded message.

It is also possible to set the rules of the comparison between two following joint insulation integrity signal received by the receiving means.

For example one of the possibility is to set the comparison with the parameter of the distance of Hamming.

In a preferred embodiment one joint insulation integrity signal is identified as identical to the following joint insulation integrity signal when less the three bit of the first one are different in respect of the second one, e.g. when the distance of Hamming is equal to 3.

According to a further improvement the train presence detection signals and communication signals are constituted by a wave, which wave presents an amplitude maximum value and an amplitude minimum value, the transmission of the joint insulation integrity signal occurring only during time interval of amplitude minimum value.

Usually in track circuits two frequency modulations are usually applied to alternate currents, at 50 Hz and 178 Hz, to allow transmission of a larger number of codes, thereby improving safety by providing more complete information to the trains, in a shorter time.

All the carrier frequencies are modulated ON/OFF, each speed code to be transmitted inside the track circuit is identified by a period of presence of a predetermined frequency and by a period of absence of the said frequency.

The transmission of the joint insulation integrity signal is done in the period of absence of other signals, in order to maintain at the lowest level the tension spikes of the entire system and in order to do not generate disturbs on the transmission lines.

According to a preferred embodiment the joint insulation integrity signal presents a carrier frequency of 500 Hz.

The choice of 500 Hz permits to operate in a range of frequencies compatible with the maximum noises admitted by the trains or similar.

As described above, the step a) is obtained by a Frequency-shift keying modulation, in which the bit with value "1" presents a carrier frequency of 525 Hz while the bit with value "0" presents a carrier frequency of 475 Hz.

Advantageously the joint insulation integrity signal is a bit coded message composed by 8 bit.

Due to the fact that the transmission of the joint insulation integrity signal according to the present invention is done during the "OFF" period of the other signals, the 8 bit messages presents a length easy to be entirely transmitted in this range of time.

According to another embodiment, the transmission of the joint insulation integrity signal comprises the step of:
  b1) transmission of the joint insulation integrity signal constituted by a bit message;
  b2) transmission of the said joint insulation integrity signal constituted by the logical complement of the said bit message.

This improvement makes the message more dynamic and it avoid errors in the detection of the signal, because the receiving units expect to receive cyclically the 8 bit message and its logical complement: no external disturb or event can reproduce this sequence, corrupting the detection relating the status of the mechanical joints.

As it appears clearly form the description above in order to identify the integrity of each mechanical joint the system uses three different parameters, the message sent must be the correct one, the carrier frequency must be the correct one and also the sequence of the messages must be the correct one.

BRIEF DESCRIPTION OF THE DRAWINGS

These and other characteristics and advantages of the invention will be more apparent from the following description of a few embodiments shown in the accompanying drawings, in which.

DETAILED DESCRIPTION OF EMBODIMENTS OF THE INVENTION

Figure 1:
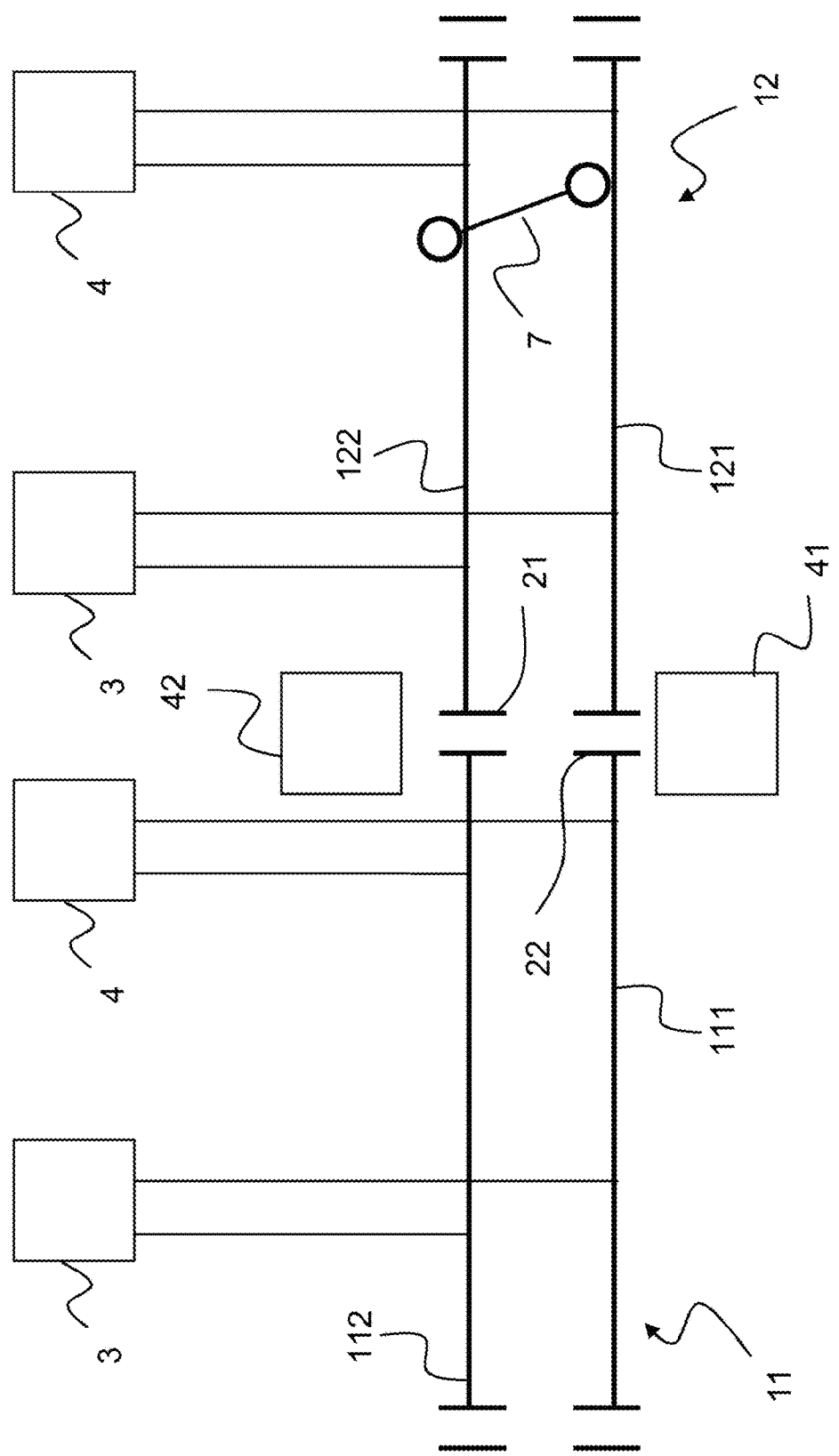
FIG. 1 shows one of the possible embodiments of a track circuit according to the prior art.

FIG. 1 shows a electrically insulating mechanical joint for track circuits according to the prior art for railway systems or the like, comprising a track segment 11 of predetermined length, which segment comprises at least two rails 111 and 112, The track segment 11 is electrically insulated from adjacent segments 12, comprising at least two rails 121 and 122, by mechanical joints 21 and 22.

The joints 21 and 22 connect together each rail 111, 112 of the track segment 11 with a corresponding rail 121, 122 belonging to adjacent track segments 12 at the ends of each track segment.

Each track segment 11 and 12 presents electric signal transmitting units 3 and receiving units 4 for transmitting and receiving train presence detection signals within the track segment 11 and/or communication signals between a train 7 and the track segment.

The track circuit illustrated in FIG. 1 and belonging to the prior art presents two further means, respectively a joint integrity transmitter 41 and a joint integrity receiver 42 to detect the integrity of the mechanical joints 21 and 22.

The integrity joint transmitter 41 inject a dedicated frequency versus the couple of mechanical joints 21 and 22, received by the joint integrity receiver 42. If the mechanical joints 21 and 22 break the receiver 42 will detect it.

As described above the track circuits belonging to the prior art requires additional means, such as, in this case, joint integrity transmitter 41 and joint integrity receiver 42, incurring in further costs and requiring to modify the configuration of the track circuit.

Figure 2:
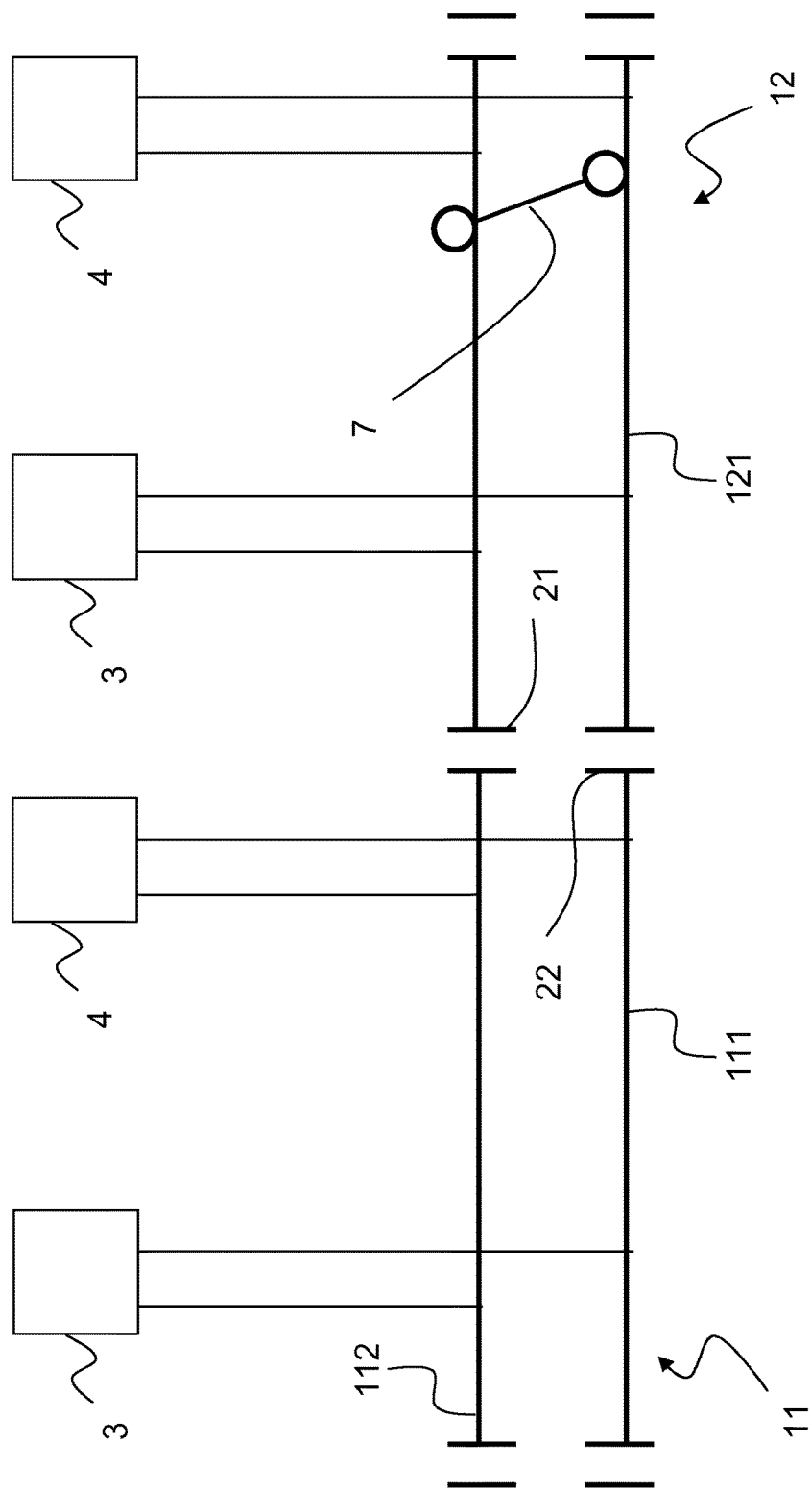
FIG. 2 shows a possible scenario in the case of a failure of a mechanical joint.

The possible scenario in the case of a failure of a mechanical joint is illustrated in FIG. 2.

A train 7 with its axles enters in the track circuit 12 and the receiver 4 connected to that track circuit, senses the shunt resistance of the train 7 and correctly put the track segment in occupied status.

In the same moment a breaking of the mechanical joint 21 occurs.

The train 7 receives the codes that is propagating from track segment 11 to track segment 12 due to the loss of insulation of the mechanical joint 21.

Figure 3:
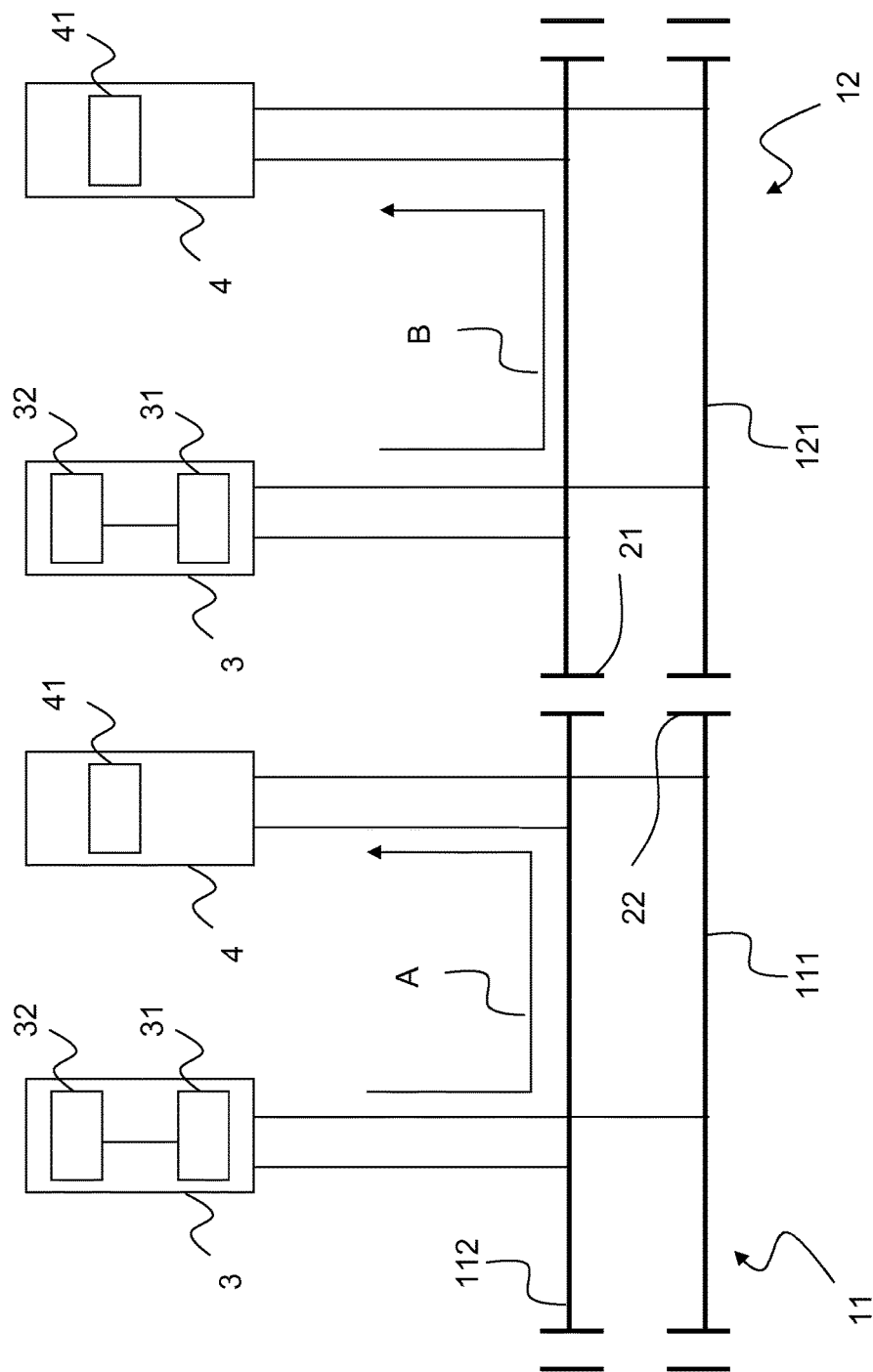
FIG. 3 shows one of the possible embodiments of the present invention.

FIG. 3 shows how the mechanical joint checker for track segments according to the present invention detect the failure of a mechanical joint.

The signals circulating in the track segments 11 and 12 comprise a further joint insulation integrity signal A, B associated to each track segment 11, 12 in order to detect the failure of the insulation of the mechanical joints 21, 22.

The joint insulation integrity signal A relating to track segment 11 is different, concerning to characteristic parameters uniquely identifying the joint insulation integrity signal of each track segment, to the integrity signal B relating to the track segment 12.

The joint insulation integrity signal A is generated and transmitted by the transmitting units 3 belonging to the track segment 11 and it is received by the receiving units 4 belonging to the track segment 11.

The joint insulation integrity signal B is generated and transmitted by the transmitting units 3 belonging to the track segment 12 and it is received by the receiving units 4 belonging to the track segment 12.

The transmitting units 3 comprise a signal generation unit 31 that generates the signals circulating in the track segment 11.

Because signals A and B are differentiated, if the mechanical joints 21 or 22 break both the receivers of track segment 11 and 12 detect the breaking of the mechanical joints 2 or 22.

In particular the receiving units 4 belonging to the track segment 11 "knows" the joint insulation integrity signal A transmitted by the corresponding transmitting units 3, and therefore if it receives a signal different from A or an attenuated one, it means that a loss of insulation occurs due to the failure of one of the mechanical joints 21 and 22.

Means for setting the track segment in a safety condition are provided.

As usual when such condition appears, an alarm signal can be sent to remote operating unit and automatically the track segments 11 and 12 are put in occupied status.

The receiving units 4 comprise an analyzing unit 41 which compares the received joint insulation integrity signal with the one that identifies the track segment 11.

The analyzing unit 41 in particular compares the characteristic parameters of the received joint insulation integrity signal with predetermined values.

The characteristic parameters analyzed are the amplitude, carrier frequency, modulation frequency and bit message content of the received signal.

The predetermined values can be set on the base of a joint insulation integrity signal A not corrupted or attenuated.

Also the discriminant to evaluate the difference between one signal and the following one can be set.

As described above, in the case the joint insulation integrity signal is a bit coded message, a message can be identified as different in respect of a following message if the second one presents a Hamming distance equal to 3 in respect of the first message.

The same consideration is valid relating to track segment 12.

Preferably the joint insulation integrity signals A and B are digital signals comprising a bit coded messages.

According to a possible embodiment of the present invention, the joint insulation integrity signal presents a carrier frequency of 500 Hz, the said signal generation unit 31 including means to generate carrier waves.

An improvement of the present invention provides that the joint insulation integrity signals A and B are obtained by a Frequency-shift keying modulation, in which the bit with value "1" presents a carrier frequency of 525 Hz while the bit with value "0" presents a carrier frequency of 475 Hz.

Advantageously the joint insulation integrity signals A and B are bit coded messages composed by 8 bit.

Furthermore, with 8 bit messages it is possible to create different type of messages according to the configuration of the track segment.

For example if the track segments are disposed like the ones of FIG. 3, it will be sufficient to provide a sequence like A-B-A-B.

If there is the need of another couple of mechanical joints, due to a ramification of the track segment 11, it will be sufficient to use another bit message C different from A and B.

With a double ramification of the track segment 11 another message D will be required.

As clearly appears from the figures the mechanical joint checker of the present invention brings to the realization of a method to detect a failure or breakage of a mechanical joint 21 or 22 inside a track segment.

This method provides the step of:
a) generation of a further joint insulation integrity signal A, B by the transmitting units 3;
b) transmission of the joint insulation integrity signal A,B by the transmitting units 3;
c) reception of the joint insulation integrity signal A, B by the receiving units 4;
d) comparison of the received joint insulation integrity signal with the one that identifies the track segment;
e) set of the said track segment 11 in a occupied status.

As previously described, the message A is transmitted by the transmitting units 3 belonging to the track segment 11 and it is received by the receiving units belonging to the track segment 11.

According to a preferred embodiment the train presence detection signals and the communication signals are constituted by a wave, which wave presents an amplitude maximum value and an amplitude minimum value, the transmission of the joint insulation integrity signal occurring only during time interval of amplitude minimum value.

In this case according to a preferred embodiment the transmitting units 3 comprise timing means 32, which timing means 32 activate the signal generation unit 31 according to predetermined timing rules.

One of the possible timing rules is the one above described, e.g. activating the generation unit during the time interval of amplitude minimum value.

The timing means allow to control the timing of the transmission of the joint insulation integrity signal A, B.

Furthermore the transmission of the joint insulation integrity signal A,B comprises the step of:
b1) transmission of the joint insulation integrity signal A, B constituted by a bit message;
b2) transmission of the joint insulation integrity signal constituted by the logical complement of the said bit message.

In this case it is possible to provide logic control units that control and set the generation of the joint insulation integrity signal.

The invention claimed is:

1. An electrically insulating mechanical joint checker for mechanical joints connecting rails of subsequent track segments of a railway line, each track segment forming part of a track circuit, comprising:
a signal transmitting unit and a receiving unit operatively coupled to each track segment for transmitting and respectively receiving train presence detection signals within said track segment and/or transmitting and respectively receiving communication signals between a train and the track segment, wherein said signal transmitting unit and receiving unit are configured to respectively transmit and receive an additional joint insulation integrity signal associated to each track segment to detect failure of insulation of said mechanical joints, wherein said signal transmitting unit and receiving unit are configured to respectively transmit and receive said joint insulation integrity signal related to the said track segment, which is different at least in respect to a joint insulation integrity signal relating to an adjacent track segment in parameters uniquely identifying the joint insulation integrity signal of each track segment, wherein said signal transmitting unit comprises a signal generation unit generating and transmitting said joint insulation integrity signal, and said signal receiving unit comprises an analyzing unit comparing a received joint insulation integrity signal with the joint insulation integrity signal that identifies the track segment, wherein said transmitting unit comprises a timing system that activates the signal generation unit according to a predetermined timing rule, wherein said signal transmitting unit and said receiving unit provide said train presence detection signals and said communication signals as a wave having an amplitude maximum value and an amplitude minimum value, and wherein said generation unit is activated by said timing system during a time interval of amplitude minimum value.

2. The electrically insulating mechanical joint checker according to claim 1, wherein said signal transmitting and receiving units are configured to transmit and receive said joint insulation integrity signal from frequency-shift keying modulation, in which a bit with value "1" presents a carrier frequency of 525 Hz while a bit with value "0" presents a carrier frequency of 475 Hz.

3. The electrically insulating mechanical joint checker according to claim 1, further comprising a system that sets the track circuit in a safety condition.

4. The electrically insulating mechanical joint checker according to claim 1, wherein said signal transmitting and receiving units are configured to transmit and receive said joint insulation integrity signal as a digital signal comprising a bit coded message.

5. The electrically insulating mechanical joint checker according to claim 4, wherein said bit coded message is composed by 8 bit.

6. The electrically insulating mechanical joint checker according to claim 1, wherein said signal transmitting and receiving units are configured to transmit and receive said joint insulation integrity signal with a carrier frequency of 500 Hz, and wherein the said signal transmitting units are configured to generate carrier waves.

7. A method of detecting a failure or breakage of a mechanical joint connecting rails of subsequent track segments of a railway line, each track segment forming part of a track circuit, wherein each track segment is operatively coupled to a signal transmitting unit and a receiving unit adapted to transmit and respectively receive train presence detection signals within said track segment and/or communications signals between a train and said track segment, the method comprising:
   (a) causing the transmitting unit to generate an additional joint insulation integrity signal, which is associated to each track segment, said joint insulation integrity signal associated with said track segment being different from the joint insulation integrity signal associated with an adjacent track segments in parameters uniquely identifying the joint insulation integrity signal of each track segment;
   (b) transmitting said joint insulation integrity signal with the said transmitting unit;
   (c) receiving said joint insulation integrity signal at said receiving unit;
   (d) comparing the received joint insulation integrity signal with the joint insulation integrity signal that identifies the track segment with said receiving unit, said transmitting unit and said receiving unit belonging to a same track segment; and
   (e) setting said track segment in an occupied status,
   further comprising the step of causing said signal transmitting and said receiving unit to transmit and receive said train presence detection signals and said communication signals as a wave having an amplitude maximum value and an amplitude minimum value,
   wherein the step of transmitting said joint insulation integrity signal occurs only during a time interval of amplitude minimum value.

8. The method according to claim 7, wherein transmitting said joint insulation integrity signal comprises transmitting said joint insulation integrity signal as a digital signal comprising a bit coded message.

9. The method according to claim 8, wherein the bit coded message is composed by 8 bit.

10. The method according to claim 8, wherein step (b) comprises the steps of:
   (b1) transmitting said joint insulation integrity signal comprising said bit coded message, and
   (b2) transmitting of said joint insulation integrity signal comprising a logical complement of said bit coded message.

11. The method according to claim 7, wherein transmitting said joint insulation integrity signal comprises transmitting said joint insulation integrity signal with a carrier frequency of 500 Hz.

12. The method according to claim 11, wherein step (a) is obtained by a Frequency-shift keying modulation, in which a bit with value "1" has a carrier frequency of 525 Hz and a bit with value "0" has a carrier frequency of 475 Hz.

* * * * *